(12) United States Patent
Young (10) Patent No.: US 9,849,248 B2
(45) Date of Patent: Dec. 26, 2017

(54) DISPENSER ASSEMBLY FOR LIQUIDS COMPRISING FLEXIBLE BARREL AND RIGID PLUNGER

(71) Applicant: Tessy Plastics Corporation, Elbridge, NY (US)

(72) Inventor: David Young, Syracuse, NY (US)

(73) Assignee: Tessy Plastics Corporation, Elbridge, NY (US)

( * ) Notice: Subject to any disclaimer, the term of this patent is extended or adjusted under 35 U.S.C. 154(b) by 172 days.

(21) Appl. No.: 14/546,489

(22) Filed: Nov. 18, 2014

(65) Prior Publication Data

US 2015/0141935 A1   May 21, 2015

Related U.S. Application Data

(60) Provisional application No. 61/905,501, filed on Nov. 18, 2013.

(51) Int. Cl.
*A61M 5/315* (2006.01)

(52) U.S. Cl.
CPC .... *A61M 5/31513* (2013.01); *A61M 5/31511* (2013.01)

(58) Field of Classification Search
CPC ................................................. A61M 5/31513

USPC ........................................................ 604/222
See application file for complete search history.

(56) References Cited

U.S. PATENT DOCUMENTS

| | | | |
|---|---|---|---|
| 4,201,209 A | 5/1980 | LeVeen et al. | |
| 4,704,105 A | 11/1987 | Adorjan et al. | |
| 5,034,002 A | 7/1991 | Duranzampa et al. | |
| 5,037,382 A | 8/1991 | Kvorning et al. | |
| 5,066,280 A | 11/1991 | Braithwaite | |
| 5,397,313 A | 3/1995 | Gross | |
| 5,411,489 A | 5/1995 | Pagay et al. | |
| 5,735,825 A | 4/1998 | Stevens et al. | |
| 5,928,202 A | 7/1999 | Linnebjerg | |
| 5,935,104 A | 8/1999 | Janek et al. | |
| 6,142,977 A | 11/2000 | Kolberg et al. | |
| 6,224,577 B1 | 5/2001 | Dedola et al. | |
| 6,342,045 B1 | 1/2002 | Somers | |
| 7,070,581 B2 * | 7/2006 | Manera ................. | A61J 7/0053 604/218 |

* cited by examiner

*Primary Examiner* — Kevin C Sirmons
*Assistant Examiner* — Deanna K Hall
(74) *Attorney, Agent, or Firm* — Barclay Damon LLP (57) ABSTRACT

A dispenser assembly is provided that has a rigid plunger with a ring-shaped protrusion. The protrusion contacts the inner wall of a flexible barrel to form a liquid-tight seal. Advantageously, the dispenser assembly does not require additional components, such as o-rings, and can be fabricated by injection molding techniques.

20 Claims, 14 Drawing Sheets

DISPENSER ASSEMBLY FOR LIQUIDS COMPRISING FLEXIBLE BARREL AND RIGID PLUNGER

CROSS-REFERENCE TO RELATED APPLICATIONS

This application is a non-provisional of U.S. Patent Application Ser. No. 61/905,501 (filed Nov. 18, 2013) the entirety of which is incorporated herein by reference.

BACKGROUND OF THE INVENTION

The subject matter disclosed herein relates to dispenser assemblies for liquids such as liquid medications. Traditional dispenser assemblies have a hollow barrel with a fitting, such as a luer fitting, at a discharge end. A plunger rod fits within the barrel and engages a sidewall of the barrel with a rubber o-ring. The rubber o-ring has ribs that extend in a radial direction outward to form a liquid seal with the barrel. These traditional dispensers are expensive to manufacture. The separate steps of forming the barrel, the plunger and the o-ring add manufacturing complexity to the overall production. The o-rings must be properly fitted to the plungers and, after assembly with the barrel, a liquid seal must be provided. This requires precision manufacturing techniques that adds to the expense of the dispenser assembly. An improved dispenser assembly that addresses at least some of these shortcomings is therefore desired. The discussion above is merely provided for general background information and is not intended to be used as an aid in determining the scope of the claimed subject matter.

BRIEF DESCRIPTION OF THE INVENTION

A dispenser assembly is provided that has a rigid plunger with a ring-shaped protrusion. The protrusion contacts the inner wall of a flexible barrel to form a liquid-tight seal. Advantageously, the dispenser assembly does not require additional components, such as o-rings, and can be fabricated by injection molding techniques.

In a first embodiment, a dispenser assembly is provided. The dispenser assembly comprises a plunger with a first diameter, the plunger formed from a first polymeric material and comprising a ring-shaped protrusion that extends in a radial direction from an outer surface of the plunger to define a second diameter, the ring-shaped protrusion being disposed proximate a distal end of the plunger, wherein the plunger has a first flexibility; and a barrel that, in an un-tensioned state, defines a third diameter, the barrel formed from a second polymeric material, different than the first polymeric material, wherein the second diameter of the ring-shaped protrusion is greater than the third diameter of the barrel, wherein the barrel has a second flexibility that is more flexible than the first flexibility such that the ring-shaped protrusion applies a force to the barrel in the radial direction to provide a liquid-tight seal between the plunger and the barrel.

In a second embodiment, a dispenser assembly s provided. The dispenser assembly consists of a plunger with a first diameter, the plunger formed from a first polymeric material and comprising a protrusion that extends in a radial direction from an outer surface of the plunger to define a second diameter, the protrusion being disposed proximate a bottom end of the plunger, wherein the plunger has a first flexibility; and a barrel that, in an un-tensioned state, defines a third diameter, the barrel formed from a second polymeric material, different than the first polymeric material, wherein the second diameter of the plunger is greater than the third diameter of the barrel, wherein the barrel has a second flexibility that is more flexible than the first flexibility such that the protrusion tensions the barrel in the radial direction to provide a liquid-tight seal between the plunger and the barrel.

In a third embodiment, a dispenser assembly is provided. The dispenser assembly consists of a plunger with a first diameter, the plunger formed from a first polymeric material and comprising a protrusion that extends in a radial direction from an outer surface of the plunger to define a second diameter, the protrusion being disposed proximate a bottom end of the plunger, wherein the plunger has a first flexural modulus, wherein the plunger, including the ring-shaped protrusion, is monolithic; and a barrel that, in an un-tensioned state, defines a third diameter, the barrel formed from a second polymeric material, different than the first polymeric material, wherein the second diameter of the plunger is greater than the third diameter of the barrel, wherein the barrel has a second flexural modulus and is more flexible than the first flexural modulus such that the protrusion tensions the barrel in the radial direction to provide a liquid-tight seal between the plunger and the barrel. The second flexural modulus of the barrel is between 500 MPa and 1200 MPa and the first flexural modulus of the plunger is at least 200 MPa more rigid than the second flexural modulus.

This brief description of the invention is intended only to provide a brief overview of subject matter disclosed herein according to one or more illustrative embodiments, and does not serve as a guide to interpreting the claims or to define or limit the scope of the invention, which is defined only by the appended claims. This brief description is provided to introduce an illustrative selection of concepts in a simplified form that are further described below in the detailed description. This brief description is not intended to identify key features or essential features of the claimed subject matter, nor is it intended to be used as an aid in determining the scope of the claimed subject matter. The claimed subject matter is not limited to implementations that solve any or all disadvantages noted in the background.

BRIEF DESCRIPTION OF THE DRAWINGS

So that the manner in which the features of the invention can be understood, a detailed description of the invention may be had by reference to certain embodiments, some of which are illustrated in the accompanying drawings. It is to be noted, however, that the drawings illustrate only certain embodiments of this invention and are therefore not to be considered limiting of its scope, for the scope of the invention encompasses other equally effective embodiments. The drawings are not necessarily to scale, emphasis generally being placed upon illustrating the features of certain embodiments of the invention. In the drawings, like numerals are used to indicate like parts throughout the various views. Thus, for further understanding of the invention, reference can be made to the following detailed description, read in connection with the drawings in which.

DETAILED DESCRIPTION OF THE INVENTION

Figures 1A, 1B:
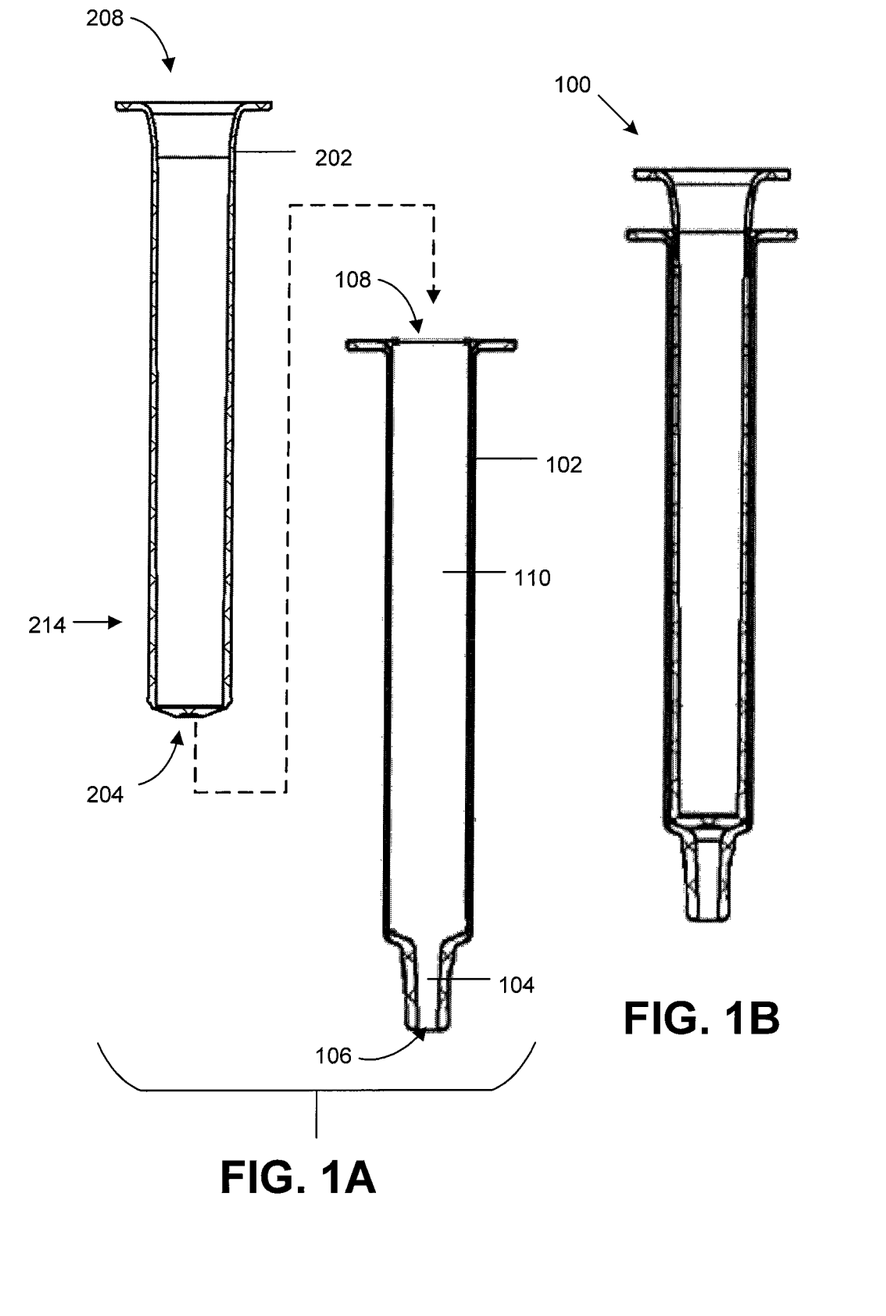
FIG. 1A provides cross section views of a plunger and a barrel.
FIG. 1B provides a cross section view of a dispenser assembly formed from the plunger and the barrel.

FIG. 1A depicts a barrel 102 and a plunger 202. The barrel 102 comprises a dispenser end 104 that provides a bottom opening 106 for withdrawing a liquid from a container. In use, the plunger 202 is inserted through a top opening 108 of the barrel 102 such that the plunger 202 is disposed inside a cavity 110. The resulting dispenser assembly 100 is depicted in FIG. 1B.

The plunger 202 is substantially rigid over its length and resists flexing in a radial direction. Flexibility may be quantified by measuring the flexural modulus according to ASTM-D790. The barrel 102 is thin-walled such that the barrel 102 will flex in the radial direction when a force is applied. Exemplary wall thickness values for the barrel 102 are between about 0.014 inches and about 0.022 inches. In one embodiment, the thickness value for the barrel 102 is between 0.017 inches and 0.019 inches. In contrast, traditional barrels are about 0.035 inches thick and are relatively rigid.

Figure 2:
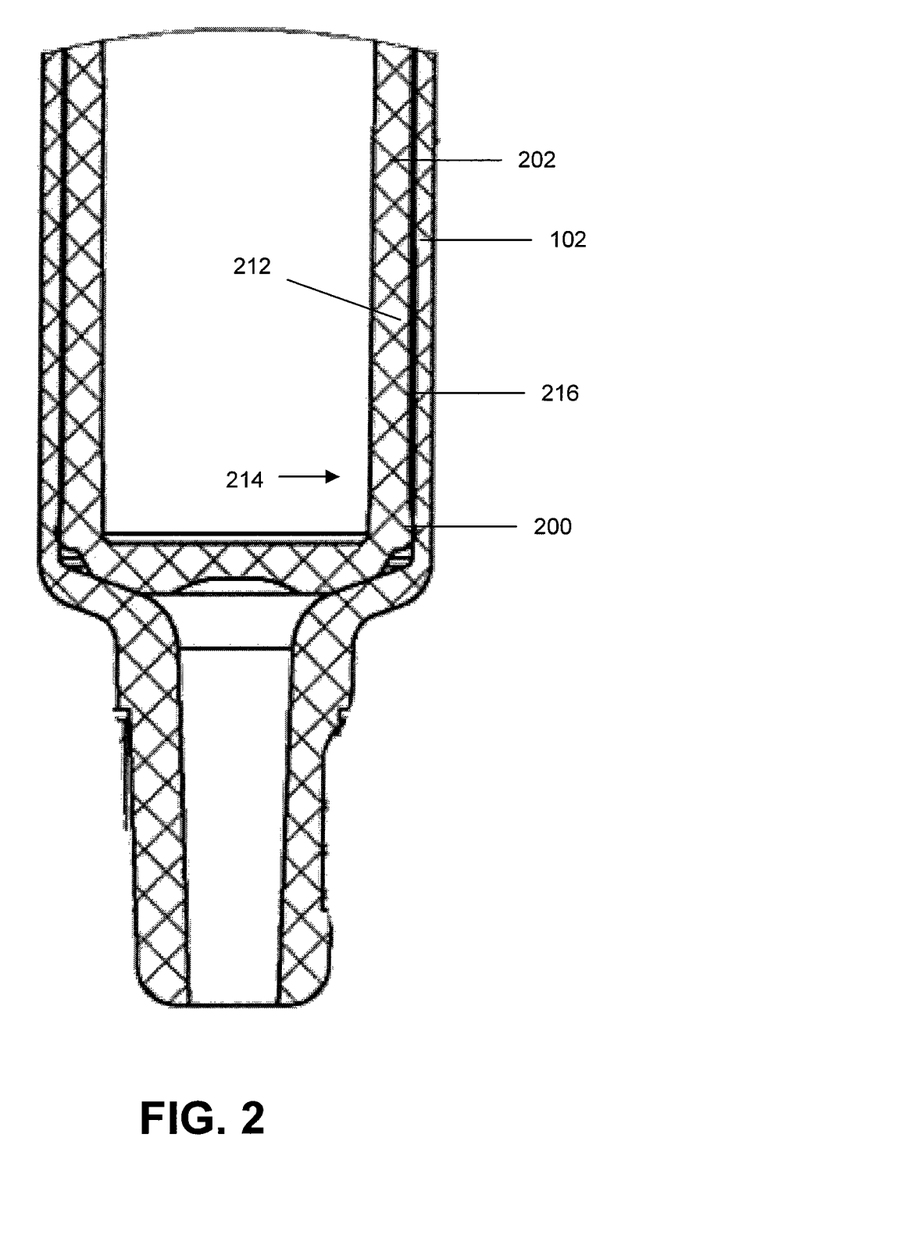
FIG. 2 is a magnified view of a portion of the dispenser assembly of FIG. 1B showing a ring-shaped protrusion.

In one embodiment, a ring-shaped protrusion 200 is disposed at a distal end 214 of the plunger 202. In one such embodiment, the ring-shaped protrusion 200 is disposed within 5 mm of a terminus of the distal end 214. As shown in FIG. 2, the ring-shaped protrusion extends from an outer surface 212 of the plunger 202 in the radial direction to define a diameter that is slightly greater than a diameter of the plunger 202. The ring-shaped protrusion 200 provides a raised bump that circumscribes the circumference of the distal end 214 of the plunger 202. The diameter defined by the ring-shaped protrusion 200 is greater than a diameter of the barrel 102 when the barrel 102 is in an un-tensioned state. As a result of the difference in diameters the ring-shaped protrusion 200 applies a force against the barrel 102 as the ring-shaped protrusion 200 passes over the length of the barrel 102. The force causes the barrel 102 to flex in the radial direction to maintain a liquid-tight seal. In one embodiment, the diameter of the plunger 202 is undercut (relative to the diameter of the barrel 102) by a predetermined amount to provide a gap 216. In one embodiment, the gap is between 0.0025 inches and about 0.010 inches. In another embodiment, the gap is between 0.004 inches and 0.008 inches. For example, the diameter of the plunger 202 may be undercut by 0.006 inches. This gap facilitates a sliding motion between the barrel 102 and the plunger 202. In one embodiment, the plunger 202 is elongated and hollow. In some embodiments, the plunger 202 comprises a top opening 208 (see FIG. 1A) that is opposite a solid end 204 such that the plunger 202 forms an elongated tube that is open at only the top opening 208. Such a hollow configuration reduces the mass of material used in fabrication of the plunger 202 and thereby reduces costs.

In one embodiment, the barrel 102 has a sufficiently high flexibility to be pulled onto the ring-shaped protrusion 200 when a vacuum is applied due to actuation of the plunger 202. For example, the dispenser end 104 may be placed into a liquid and the plunger 202 withdrawn to produce a vacuum within the barrel 102. The vacuum not only draws the liquid into the barrel 102 but also assists in the compression of the barrel 102 onto the ring-shaped protrusion 200. When the liquid is dispensed by pushing the plunger 202 downward, a higher pressure is produced that is of a sufficiently low intensity to maintain a liquid-tight seal and prevent leaks while dispensing the liquid. Advantageously, no additional sealing components (e.g. rubber rings) are needed.

The flexibility of the plunger and barrel may be quantified using any suitable technique such as ASTM International Standard Test Methods for Flexural Properties of Unreinforced and Reinforced Plastics and Electrical Insulating Materials D790.

Figure 3A:
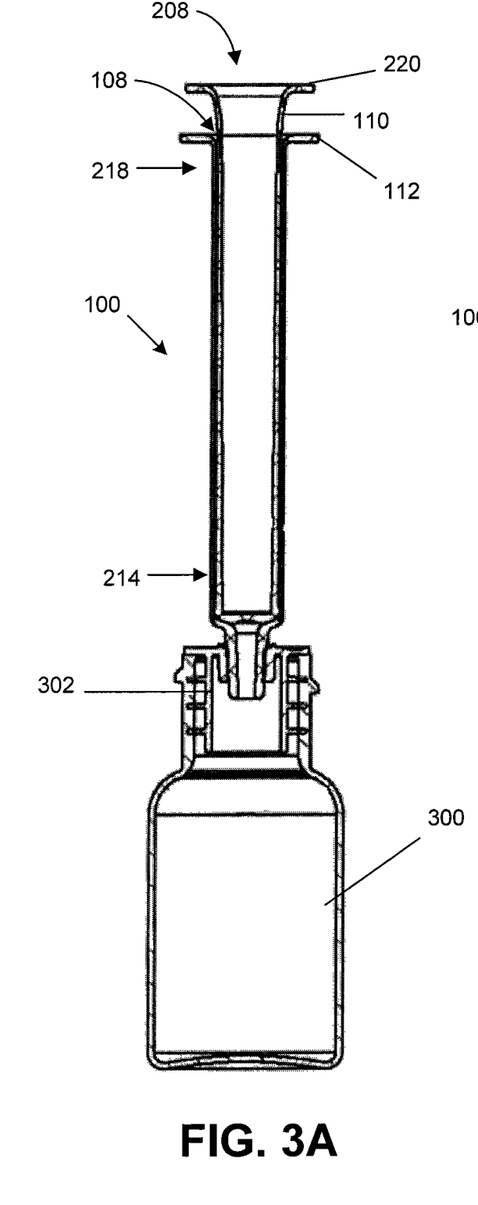
FIG. 3A is a cross section view of the dispenser assembly engaging a container.
Figure 3B:
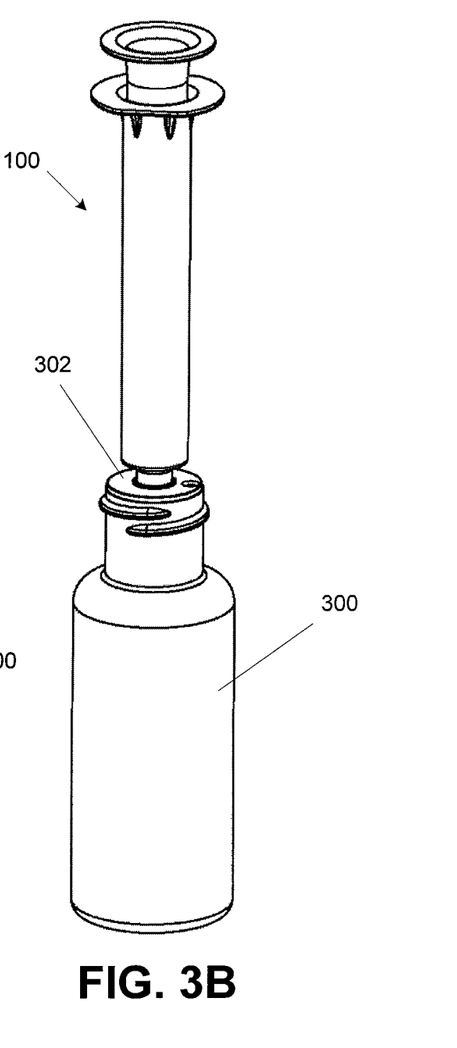
FIG. 3B is a perspective view of the dispenser assembly engaging the container.
Figure 4A:
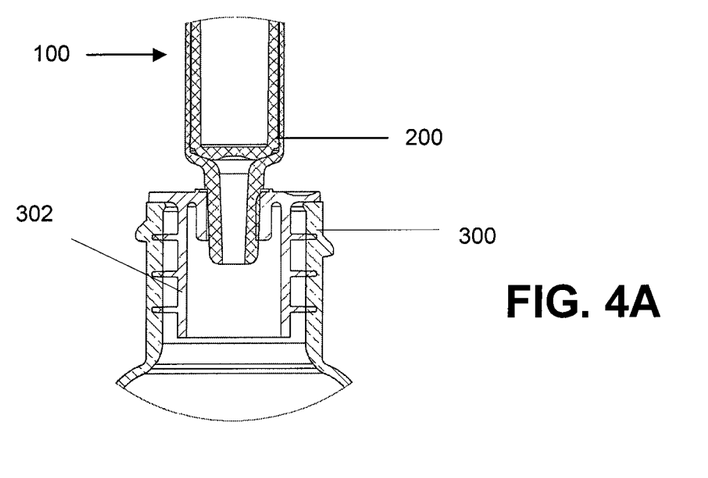
FIG. 4A is a magnified view of a portion of the dispenser assembly of FIG. 3A engaging the container, wherein the dispenser assembly is shown in a compressed state.
Figure 4B:
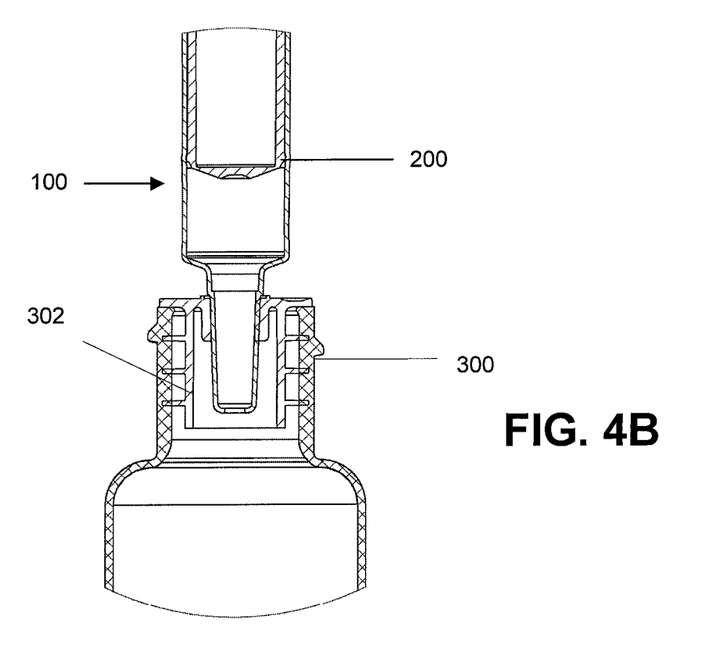
FIG. 4B is a magnified view of a portion of the dispenser assembly of FIG. 3A engaging the container, wherein the dispenser assembly is shown in a partially withdrawn state.

FIG. 3A and FIG. 3B depict two views of the dispenser assembly 100 when connected to a container 300. In the depicted embodiment, the container 300 is fitted with a press-in-bottle-adapter (PIBA) 302 that is disposed within a mouth of the container 300. FIG. 3B is a perspective view of this configuration while FIG. 3A is a cross section view. FIG. 4A is a close-up view of a connection point of FIG. 3A wherein the dispenser assembly 100 is show in a compressed state. FIG. 4B is a close-up view of the connection point of FIG. 4A wherein the dispenser assembly 100 is shown in a partially withdrawn state.

Figures 5A, 5B:
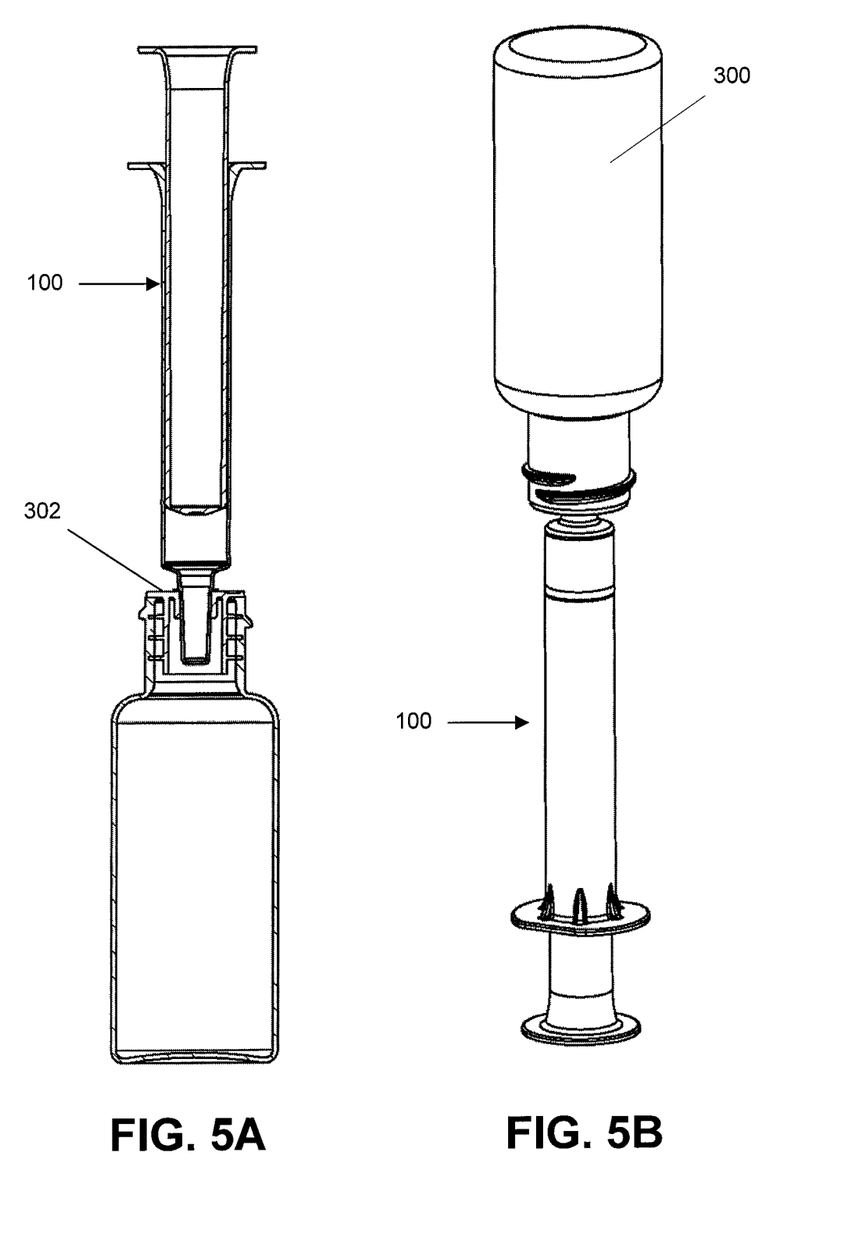
FIG. 5A is a cross section view of the dispenser assembly that is similar to FIG. 3A, except in that the dispenser assembly is shown in a partially withdrawn state.
FIG. 5B is a perspective view of the dispenser assembly engaging the container in an inverted state.

FIG. 5A is a cross section view of the dispenser assembly 100 engaging the PIBA 302 to form a liquid-tight seal between the dispenser assembly 100 and the PIBA 302. FIG. 5B shows the container 300 and the dispenser assembly 100 in an inverted state. The inverted state facilitates the remove of liquid from the container 300.

Figure 6A:
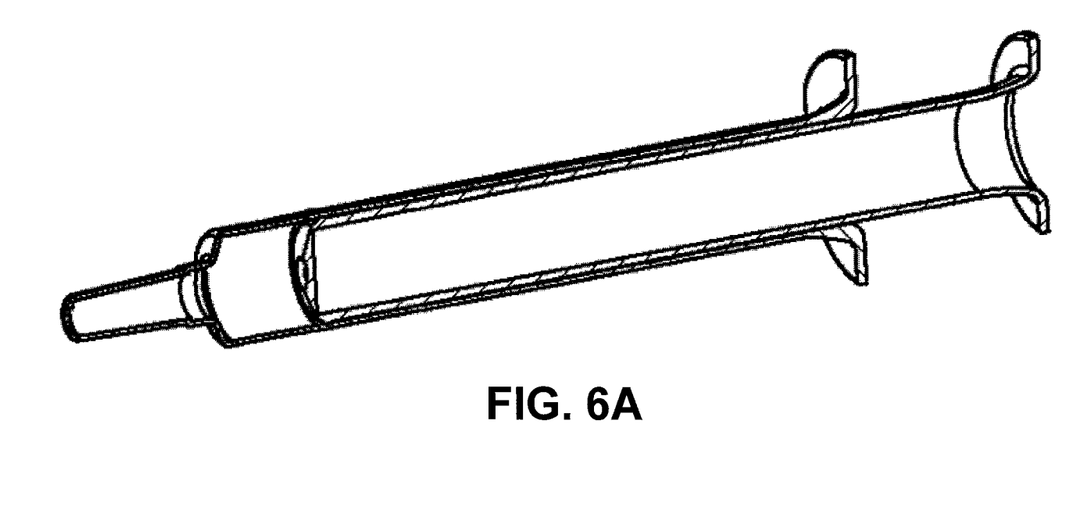
FIG. 6A is a cross section view of the dispenser assembly is shown in a partially withdrawn state.
Figure 6B:
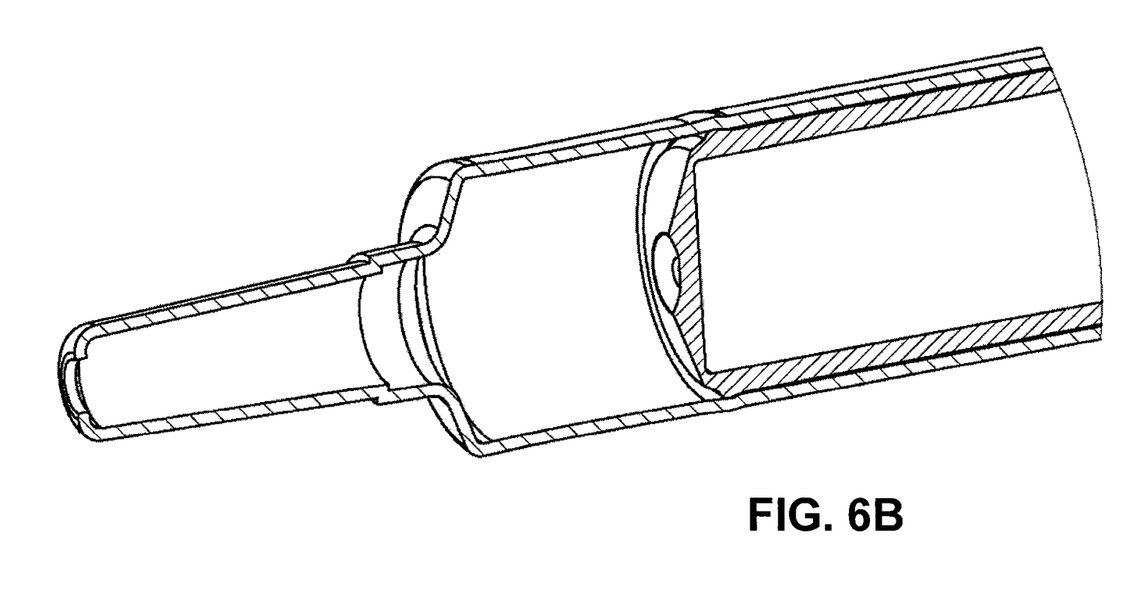
FIG. 6B is a magnified view of a portion of the dispenser assembly of FIG. 6A.
Figure 6C:
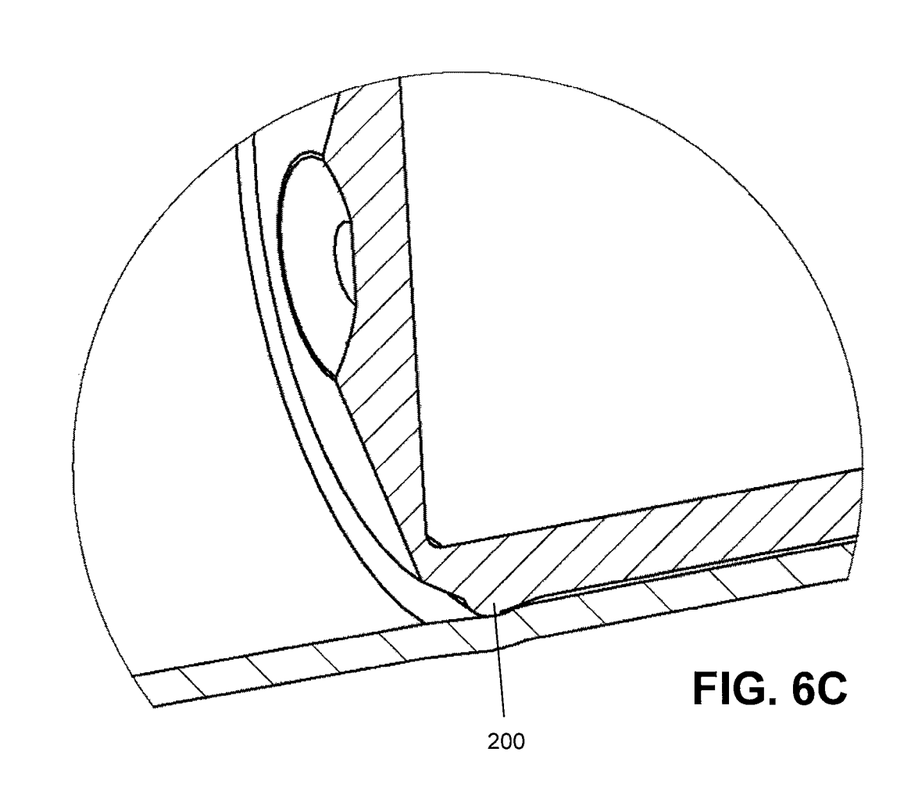
FIG. 6C is a magnified view of a portion of the dispenser assembly of FIG. 6B.

FIG. 6A, FIG. 6B and FIG. 6C are cross section views of the dispenser assembly in a partially withdrawn state shown at different magnifications. In FIG. 6C, the ring-shaped protrusion 200 is labeled for the sake of illustration.

Figure 7A:
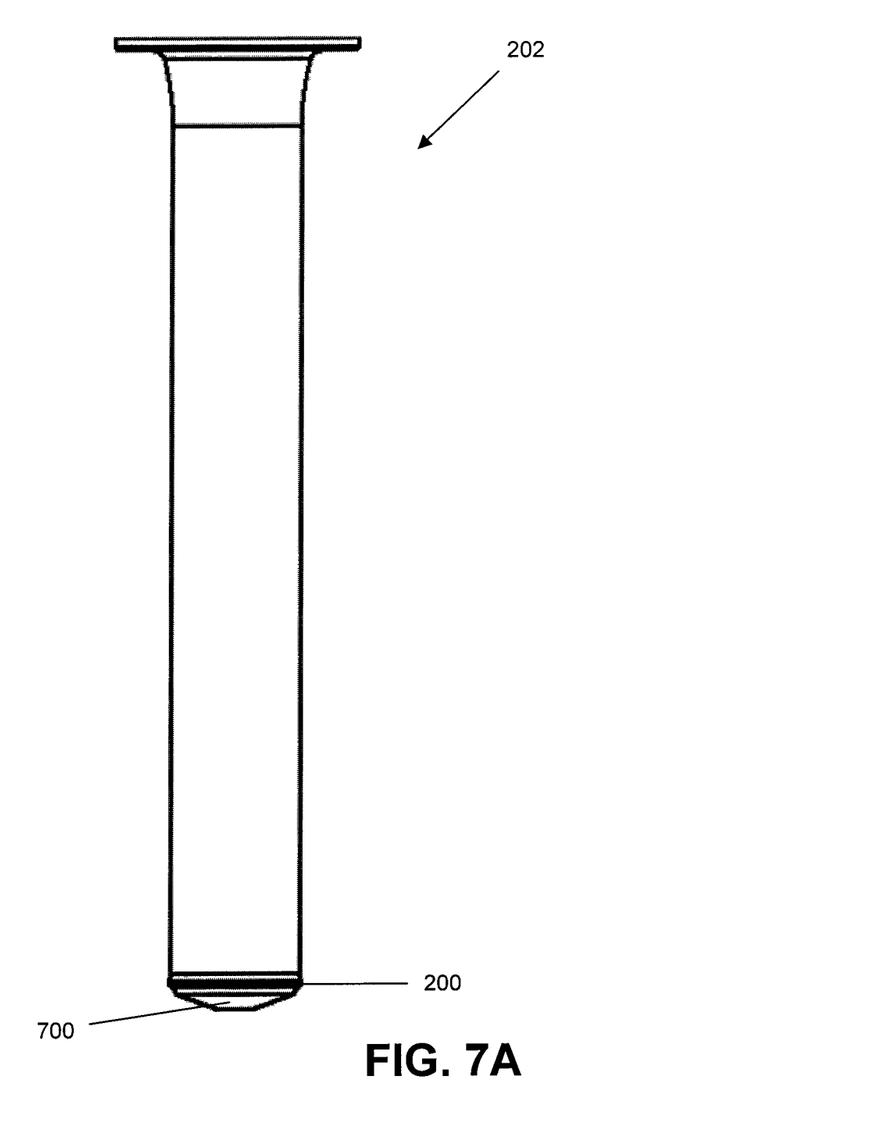
FIG. 7A is a side view of an exemplary plunger.
Figure 7B:
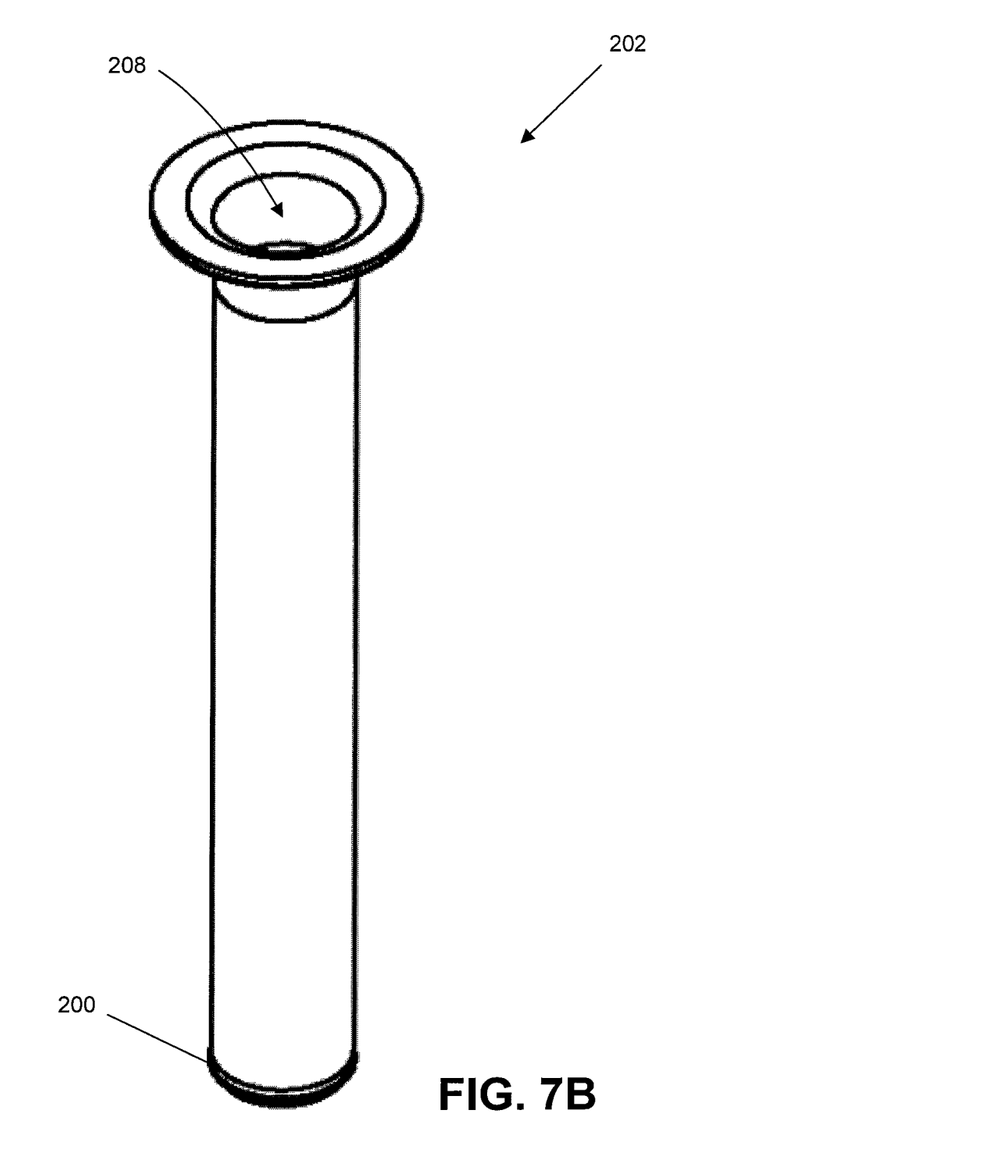
FIG. 7B is a top perspective view of an exemplary plunger.
Figure 7C:
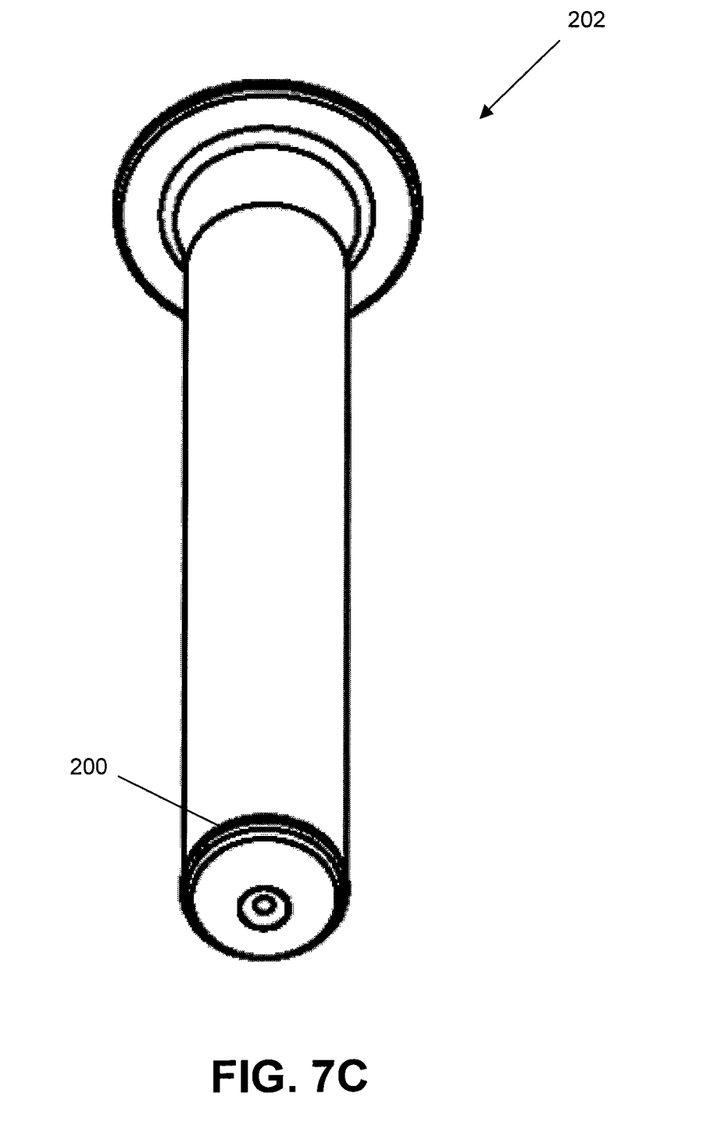
FIG. 7C is a bottom perspective view of an exemplary plunger.
Figure 7D:
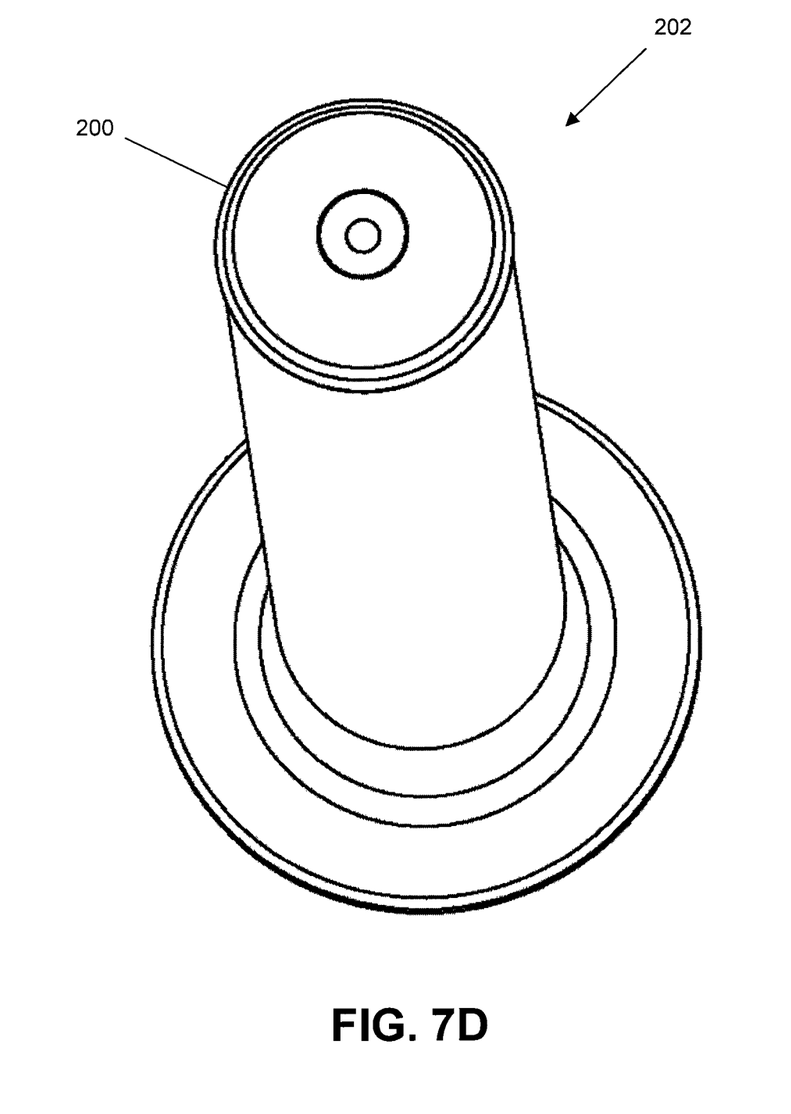
FIG. 7D is another bottom perspective view of an exemplary plunger.
Figure 7E:
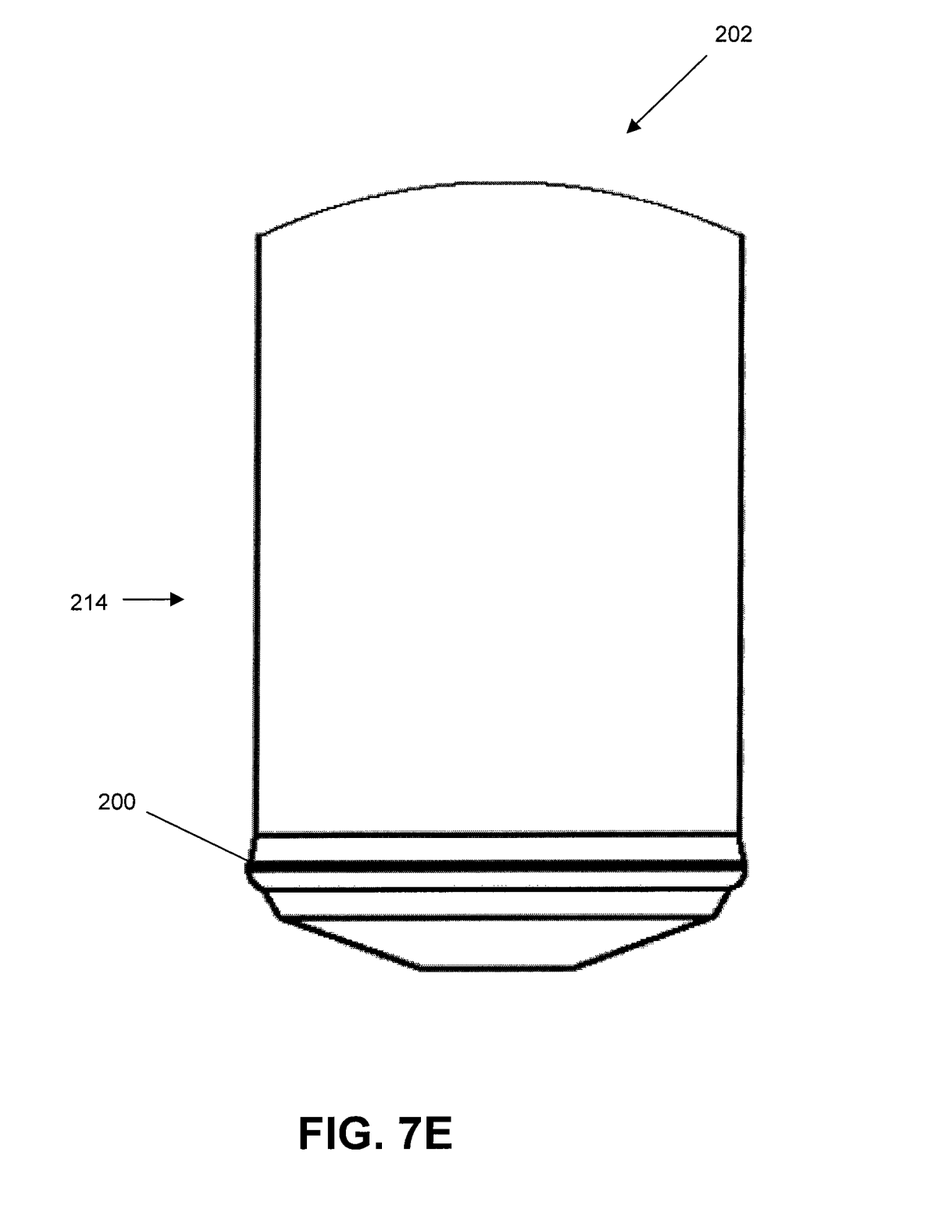
FIG. 7E is a side view of a distal end of an exemplary plunger.
Figure 7F:
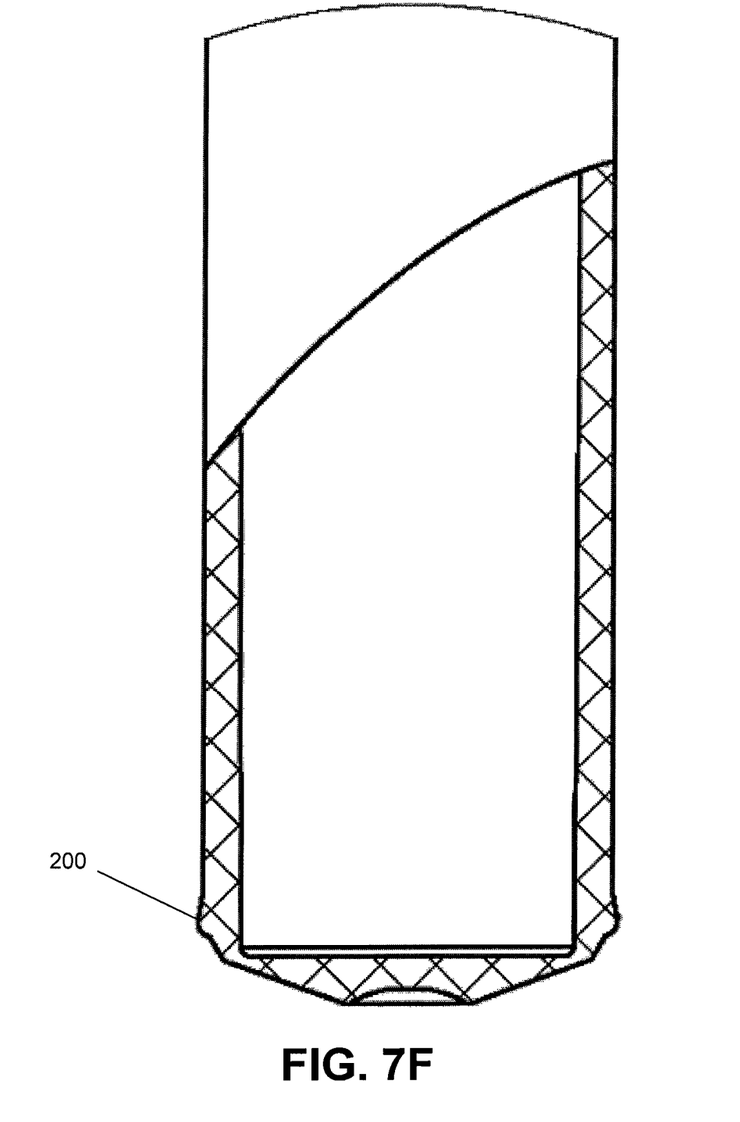
FIG. 7F is a cross section view of the distal end of FIG. 7E.

FIG. 7A is a side view of the plunger 202 showing the ring-shaped protrusion 200. In FIG. 7A, a conical tip 700 is depicted that mates with a corresponding shape on the barrel 102. FIG. 7B is a top perspective view of the plunger 202 illustrating both the top opening 208 and the ring-shaped protrusion 200. FIG. 7C is a bottom perspective view of the plunger 202 showing the ring-shaped protrusion 200. FIG. 7D is another bottom perspective view of the plunger 202 showing the ring-shaped protrusion 200. FIG. 7E is a side view of the distal end 214 of the plunger 202 showing the ring-shaped protrusion 200. FIG. 7F is a cross section view of the distal end of FIG. 7E.

In some embodiments, a proximal end 218 of the plunger 202, which is opposite the distal end 214, comprises a plunger flange 220. The plunger flange 220 is proximate the top opening 208 of the plunger 202. In such an embodiment, the plunger flange 220 provides a receptacle for a user's finger and/or thumb during operation of the dispenser assembly 100. Likewise, in some embodiments, the barrel 102 comprises a barrel flange 112 proximate the top opening 108 of the barrel 102 that provides a receptacle for the user's finger and/or thumb during operation of the dispenser assembly 100.

In one embodiment, the dispenser assembly 100 is formed by injection molding. In one embodiment, the plunger 202 and/or the barrel 102 consists of only the polymeric material and lacks additional components (e.g. a rubber o-ring). Such a configuration is conducive to forming the plunger 202 and/or barrel 102 by injection molding which streamlines production of the dispenser assembly 100 and reduces costs. In one such embodiment, the plunger 202 and barrel 102 are respectively formed by injection molding from different polymeric materials. For example, the plunger may be formed from high density polyethylene (HDPE) while the barrel is formed of polypropylene (PP). A suitable polypropylene is a polypropylene random copolymer sold by EXXONMOBIL™ under the brand name PP9074MED. PP9074MED has a tensile strength at yield (510 mm/min) of about 32.8 MPA, a tensile strength at break (510 mm/min) of about 17.2 MPa, an elongation at yield (510 mm/min) of about 13%, an elongation at break (510 mm/min) of about 51% and a flexural modulus (1% secant, 1.3 mm/min) of about 1050 MPa (measured according to ASTM D790). In one embodiment, the barrel 102 has a flexural modulus of less than 1200 MPa while the plunger has a flexural modulus of more than 1200 MPa. In another embodiment, the flexural modulus of the barrel is between 500 MPa and 1200 MPa. In one such embodiment, the difference in flexural modulus of the barrel and the plunger is at least 100 MPa. In another embodiment, the difference is at least 300 MPa. In yet another embodiment, the difference is at least 500 MPa. The use of different polymeric materials in the plunger and barrel, respectively, provides natural lubricity and thereby promotes the operation of the dispenser assembly 100. In one embodiment, the plunger 202, including the ring-shaped protrusion, is monolithic. In another embodiment, the barrel 102 is monolithic.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A dispenser assembly comprising:
   a plunger with a first diameter, the plunger formed from a first polymeric material and comprising a rigid ring-shaped protrusion that extends in a radial direction from an outer surface of the plunger to define a second diameter, the rigid ring-shaped protrusion being disposed proximate a distal end of the plunger, wherein the plunger has a first flexibility; and
   a barrel formed from a second polymeric material that is different than the first polymeric material, the barrel being configured to flex outward in response to a radial force applied by the rigid ring-shaped protrusion, and wherein a portion of the barrel is compressed onto the rigid ring-shaped protrusion to provide a liquid-tight seal between the plunger and the barrel.

2. The dispenser assembly as recited in claim 1, wherein the first diameter of the plunger is less than a third diameter of the barrel such that the plunger is undercut relative to the barrel.

3. The dispenser assembly as recited in claim 1, wherein the plunger is undercut, relative to the barrel, by between 0.0025 inches and about 0.010 inches.

4. The dispenser assembly as recited in claim 1, wherein the plunger is undercut, relative to the barrel, by between 0.0025 inches and about 0.010 inches and the rigid ring-shaped protrusion extends in the radial direction from the outer surface of the plunger by a distance between 0.0025 inches and about 0.010 inches to define the second diameter.

5. The dispenser assembly as recited in claim 1, wherein the plunger is a hollow tube that comprises a top opening.

6. The dispenser assembly as recited in claim 1, wherein the plunger is a hollow tube that comprises a top opening and the barrel comprises a barrel wall with a first thickness, the plunger comprises a plunger wall with a second thickness, and the first thickness is less than the second thickness such that the barrel wall is more flexible than the plunger wall.

7. The dispenser assembly as recited in claim 1, wherein the first polymeric material is high density polyethylene (HDPE) and the second polymeric material is polypropylene (PP).

8. The dispenser assembly as recited in claim 1, wherein the plunger consists of the first polymeric material such that the plunger is free of o-rings.

9. The dispenser assembly as recited in claim 1, further comprising a plunger flange proximate a top opening of the plunger.

10. The dispenser assembly as recited in claim 1, further comprising a barrel flange proximate a top opening of the barrel.

11. The dispenser assembly as recited in claim 1, wherein the plunger, including the rigid ring-shaped protrusion, is monolithic.

12. The dispenser assembly as recited in claim 1, wherein the second polymeric material has a flexural modulus of less than 1200 MPa.

13. The dispenser assembly as recited in claim 1, wherein the second polymeric material has a flexural modulus between 500 MPa and 1200 MPa.

14. The dispenser assembly as recited in claim 1, wherein the first polymeric material has a first flexural modulus and the second polymeric material has a second flexural modulus, the second flexural modulus being between 500 MPa and 1200 MPa and the first flexural modulus is at least 200 MPa different from the second flexural modulus.

15. The dispenser assembly as recited in claim 1, wherein the first polymeric material has a first flexural modulus and the second polymeric material has a second flexural modulus, the second flexural modulus being between 500 MPa and 1200 MPa and the first flexural modulus is at least 500 MPa different from the second flexural modulus.

16. The dispenser assembly as recited in claim 1, wherein the barrel has a wall thickness between about 0.014 inches and about 0.022 inches.

17. The dispenser assembly as recited in claim 1, wherein the barrel has a wall thickness between about 0.017 inches and about 0.019 inches.

18. A dispenser assembly consisting of:
- a plunger with a first diameter, the plunger formed from a first polymeric material and comprising a rigid protrusion that extends in a radial direction from an outer surface of the plunger to define a second diameter, the rigid protrusion being disposed proximate a bottom end of the plunger, wherein the plunger has a first flexibility; and
- a barrel formed from a second polymeric material defining a third diameter that is greater than the first diameter, wherein the barrel has a second flexibility that is more flexible than the first flexibility and is configured to flex outward when the rigid protrusion tensions the barrel in the radial direction to define a diameter that is larger than the third diameter, and provide a liquid-tight seal between the plunger and the barrel.

19. The dispenser assembly as recited in claim 18, wherein the first polymeric material has a first flexural modulus and the second polymeric material has a second flexural modulus, the second flexural modulus being between 500 MPa and 1200 MPa and the first flexural modulus is at least 500 MPa different from the second flexural modulus.

20. A method of forming a seal between a plunger having a rigid annular protrusion and a flexible hollow barrel having an inner wall, the method comprising:
- inserting the plunger into the flexible hollow barrel; and
- contacting the inner wall of the flexible hollow barrel with the rigid annular protrusion;
- wherein a portion of the flexible hollow barrel is pulled onto the rigid annular protrusion when a vacuum is applied due to actuation of the plunger, the vacuum assisting in compressing the portion of the flexible hollow barrel onto the rigid annular protrusion.

* * * * *